United States Patent
DeCosmo et al.

(10) Patent No.: US 11,920,746 B2
(45) Date of Patent: Mar. 5, 2024

(54) FLAMELESS LED CANDLE WITH FLICKERING EFFECT AND FAN-DRIVEN SCENT DIFFUSER

(71) Applicant: Ulta-Lit Tree Company, Glenview, IL (US)

(72) Inventors: John DeCosmo, Glenview, IL (US); James L. Howard, Bloomingdale, IL (US)

(73) Assignee: ULTA-LIT TREE COMPANY, Glenview, IL (US)

( * ) Notice: Subject to any disclaimer, the term of this patent is extended or adjusted under 35 U.S.C. 154(b) by 315 days.

(21) Appl. No.: 17/356,957

(22) Filed: Jun. 24, 2021

(65) Prior Publication Data

US 2022/0412525 A1    Dec. 29, 2022

(51) Int. Cl.

| | |
|---|---|
| F21S 10/04 | (2006.01) |
| A61L 9/12 | (2006.01) |
| F21S 6/00 | (2006.01) |
| F21S 9/02 | (2006.01) |
| F21V 3/02 | (2006.01) |
| F21V 23/04 | (2006.01) |

(52) U.S. Cl.
CPC ............ *F21S 10/043* (2013.01); *A61L 9/122* (2013.01); *A61L 9/127* (2013.01); *F21S 6/001* (2013.01); *F21S 9/02* (2013.01); *F21V 3/02* (2013.01); *F21V 23/04* (2013.01)

(58) Field of Classification Search
CPC . F21S 10/043; F21S 6/001; F21S 9/02; A61L 9/122; A61L 9/127; F21V 3/02; F21V 23/04

USPC ......................................................... 362/101
See application file for complete search history.

(56) References Cited

U.S. PATENT DOCUMENTS

| | | |
|---|---|---|
| 7,093,949 B2 | 8/2006 | Hart |
| 7,633,232 B2 | 12/2009 | Wong |
| 7,695,171 B2 | 4/2010 | Lederer |
| 8,412,029 B2 | 4/2013 | Browder |
| 9,625,112 B2 | 4/2017 | Li |
| 2008/0036332 A1 | 2/2008 | Helf |
| 2014/0304903 A1* | 10/2014 | Cogswell ............... E03D 9/052 4/314 |
| 2015/0108241 A1* | 4/2015 | Chase .................... A61L 9/122 239/398 |

(Continued)

*Primary Examiner* — Andrew J Coughlin
*Assistant Examiner* — Hana S Featherly
(74) *Attorney, Agent, or Firm* — Ice Miller LLP; Justin D. Swindells (57) ABSTRACT

A flameless electric candle having a fan-driven scent diffuser. The candle includes a body portion having a translucent portion and a generally elongated cylindrical shape and housing therein a light emitting device configured to permit its emitted light to be partially visually discernible through the translucent portion. There is below the body portion, a base portion that includes a PCB, a switch, a light emitting device, a power source, a fan oriented to force air in a downwards direction away from the body portion, a pad configured to receive upon a surface thereof a fragrance or scent, openings in a wall of the base portion to allow the forced air scented by the fragrance to escape the base portion. The switch is selectable among a first mode in which the LED and fan are both on, an off mode both the LED and fan are off, and a second mode wherein only one of the LED or fan is on.

19 Claims, 9 Drawing Sheets

(56) References Cited

U.S. PATENT DOCUMENTS

| | | | |
|---|---|---|---|
| 2015/0147707 A1* | 5/2015 | Hatfield | A61L 9/037 |
| | | | 431/289 |
| 2016/0356442 A1 | 12/2016 | Garcia | |
| 2017/0122541 A1 | 5/2017 | Patton | |
| 2018/0292058 A1* | 10/2018 | Li | A61L 9/03 |
| 2019/0195447 A1* | 6/2019 | Wu | B05B 1/14 |

* cited by examiner

FIG. 9

# FLAMELESS LED CANDLE WITH FLICKERING EFFECT AND FAN-DRIVEN SCENT DIFFUSER

FIELD OF THE INVENTION

The present disclosure relates to LED candles and scent diffusers, and, more particularly, to an apparatus that combines an LED candle with a fan-driven scent diffuser.

BACKGROUND OF THE INVENTION

Flameless candles incorporate a light emitting diode to simulate a flame and can produce a flickering effect to further cement the illusion of a real flame. Scent diffusers usually involve a heating element and an electrical source of sufficient energy output to power the heating element. Some attempts have been made to combine flameless candles with an actively powered scent diffuser, but these suffer from various drawbacks including complexity, high power draw, too faint a scent, an external power source, failing to resemble a real candle, and how the fragrance or scent is directed. A need exists for an improved flameless candle illuminated by a light emitting device with a fan-driven scent diffuser that does not suffer from these and other drawbacks. The present disclosure address this and other needs.

SUMMARY OF THE INVENTION

It should be noted that the term "candle" as used herein refers to a structure that is designed to resemble a traditional wax candle in color, shape, size, and/or texture, and includes an electrically powered light (e.g., an electrically powered light emitting device such as a light emitting diode or LED) that is configured to simulate a flame of a traditional wax candle. In some embodiments of the present disclosure, the "flame" or electric light can be arranged in an interior of the body of the candle so that the light emanates from within the body of the candle as opposed to simulating an exposed flame. The brightness of the interior light can be made to undulate to simulate a flickering effect as produced by a real flame. The term flameless refers to the absence of a real fire flame, which is substituted by an electric light that simulates light produced by a real flame.

The candle disclosed herein also features a fan-driven scent diffuser that wisps scented or fragranted air quietly away from the body of the candle into its environment. The combination of an interior lighting effect inside the empty body or cavity of the candle and the invisible actively driven emission of scented air from the candle creates a special visual and olfactory effect and reduces space and uses less power compared to a separate actively powered scent diffuser. An air of mystery is presented in the candle through the combination of an unexposed flame effect created inside almost the entire empty body of the candle and invisible scent emanating from the candle. The environment around the candle is infused with the scent, and the majority of the body of the candle is illuminated from within without creating any shadows or other visible artifacts that would be visible if components were introduced into the cavity of candle's body. The scent, which can be infused or incorporated into an oil-based liquid, can be easily refilled without spilling or coming into contact with the user's hand or fingers. The fan, which is whisper quiet and barely audibly perceptible, is oriented to blow air in a downwards direction across a pad on which the scent is disposed, turn 90 degrees, and then exit openings that lead away from the candle's base to the outside environment.

According to an embodiment of the present disclosure, a flameless electric candle having a fan-driven scent diffuser is disclosed. The candle includes: a body portion having a translucent portion and a generally elongated cylindrical shape and housing therein a light emitting device configured to permit its emitted light to be partially visually discernible through the translucent portion; and a base portion below the body portion. The base portion includes: an electronics module having a printed circuit board (PCB), a switch, the light emitting device, and a power source configured to supply power to the PCB and the light emitting device; a fan coupled to the PCB and powered by the power source, the fan being oriented to force air in a downwards direction away from the body portion; a pad configured to receive upon a surface thereof a fragrance or scent, the pad being positioned below the fan such that the forced air moves toward the pad; a plurality of openings in a wall of the base portion to allow the forced air scented by the fragrance or scent to escape the base portion. The switch is selectable among one of a plurality of modes, the modes including a first mode wherein the light emitting device and the fan are turned on, an off mode wherein neither the light emitting device nor the fan is turned on, and a second mode wherein one of the light emitting device or the fan is turned on.

The base portion can include a wall portion that contains the PCB and the power source so that when the light emitting device is emitting light, neither the PCB nor the power source is visible through the transparent portion. The base portion can further include a post arranged in the center of the base portion, the light emitting device being positioned on the post so that the light emitting device can be positioned in a generally central area inside the body portion at a height corresponding to a height of the post.

The post can be flexible to sway from side to side, and the fan can be rotationally unbalanced to cause the post to wobble as the fan rotates, thereby inducing the post to sway or undulate from side to side, creating a dynamic lighting effect via the translucent portion of the body portion. The PCB can be configured to cause the light emitting device to periodically or randomly change an intensity or brightness output of light emitted by the light emitting device to create a flickering effect through the translucent portion.

The candle can further include a wick element extending away from a top portion of the body portion, with light emitted by the light emitting device appearing to emanate from within the interior of the body portion. The wick element can be arranged in a recess portion of the body portion such that the top portion away from which the wick element extends can be located a distance below a top surface of the body portion.

The power source can be a rechargeable Lithium-Ion battery, the base portion further including a power charging interface configured to receive a plug for recharging the battery from an external power supply. The PCB can be further configured to adjust a speed of the fan or a duty cycle of the fan to reduce power consumption from the power source. The base portion can include a twist and lock feature to removably secure the base portion and the body portion.

The candle can further include a safety switch arranged to change states in response to the twist and lock feature being engaged, the change of states causing energy to be supplied or stopped from the power source. The PCB can be configured to turn off the fan even when the switch is in the first or second mode, in response to detecting that a current or a voltage of the power source falls below a predetermined threshold.

The plurality of modes can further include a third mode that determines whether light emitted by the light emitting device is steady or is made to appear to flicker. The candle can further include a second light emitting device in the body portion, and the PCB can be configured to provide power to one or both of the light emitting device and the second light emitting device.

The base portion can further include a first post arranged in the center of the base portion, the light emitting device can be positioned on the first post so that the light emitting device is positioned in a generally central area inside the body portion at a height corresponding to a height of the first post, and the base portion can include a second post on which the second light emitting device is positioned, the first post can have a different height relative to the second post so that the light emitting device and the second light emitting device can be at different heights within the base portion.

A combination is also disclosed including the candle disclosed herein and a container, cartridge, or substrate containing the fragrance or scent. The container or cartridge can contain the fragrance or scent incorporated into an oil-based liquid. The container can include an eye dropper having a pipette and a bulb to draw the oil-based liquid into the pipette by squeezing the bulb and to release the oil-based liquid from the eye dropper by releasing the bulb.

The pad can include a felt material and has a generally thin, donut shape. The air moved by the fan can be configured to travel in a first direction from the fan toward the pad, strike the pad, and change direction to a second direction before exiting the plurality of openings, the first direction being generally orthogonal to the second direction, and the plurality of openings being spaced around a periphery of the base portion so that the air exits the base portion to create a 360 degree fragrance field around the candle.

The fan can include multiple fan blades arranged on a bottom surface of a fixed portion of the fan to direct air away from the fixed portion toward a bottom of the base portion.

The above summary is not intended to represent each implementation or every aspect of the present disclosure. Additional features and benefits of the present disclosure are apparent from the detailed description and figures set forth below.

BRIEF DESCRIPTION OF THE DRAWINGS

The foregoing and other advantages of the invention will become apparent upon reading the following detailed description and upon reference to the drawings.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION OF THE INVENTION

Figure 1:
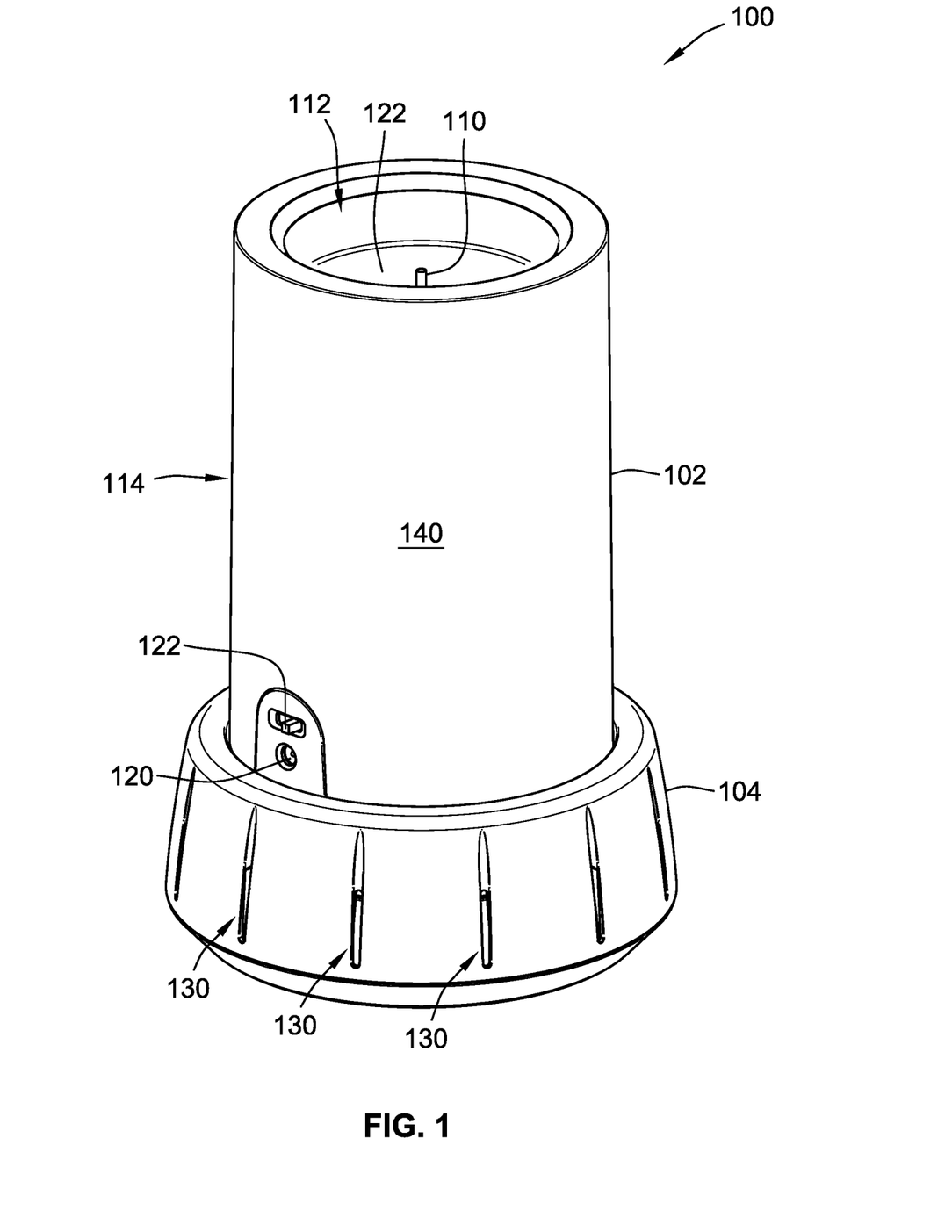
FIG. 1 is a perspective view of a candle exploded into a body portion and a base portion below the body portion.

FIG. 1 illustrates a fully assembled flameless electric candle having a fan-driven scent diffuser 100. The candle includes a body portion 102 and a base portion 104 below the body portion 102. The body portion 102 has a translucent portion 114 and a generally elongated cylindrical shape to resemble a candle. The housing 140 of the body portion 102 houses therewithin one or more light emitting devices 300 or 500*a*, 500*b* (best seen in FIGS. 3 and 5), such as light emitting diodes or LEDs. Each light emitting device 300, 500*a*, 500*b* is configured to permit its emitted light to be partially visually discernible through the translucent portion 114 of the body portion 102.

Below the body portion 102, a base portion 104 is provided. In general, the body portion 102 houses the light emitting components of the candle 100, and the base portion 104 houses the components involved in driving scent from the candle 100. The terms "above" and "below" herein are intended with reference to earth. For example, when the candle 100 is resting upon its base on a horizontal surface, relative to earth or ground, "below" refers to a direction toward earth, and "above" refers to a direction away from earth. The candle 100 is configured to rest in an upright position as shown in, e.g., FIG. 1, with the body portion 102 resting against the base portion 104 by operation of gravity.

The base portion 104 generally includes an electronics module having a printed circuit board (PCB) (not shown for ease of illustration), a switch 122, the light emitting device (s) 300, 500*a*, 500*b*, and a power source 302 (best seen in FIG. 3), which is configured to supply power to the PCB and the light emitting device(s) 300, 500*a*, 500*b*. Note that for ease of illustration to avoid obscuring other structural details of the candle 100, the PCB is not shown in FIG. 3, and neither are the wires, which would connect the various electronic components together and to the power source 302. Preferably, although not necessarily, the PCB is positioned within a raised wall 200 (see FIGS. 2 and 3) of the base portion 104. This raised wall 200 together with a lower portion 320 (FIG. 3) of the body portion 102 can create a relatively opaque area of the candle 100 so that the PCB and other components housed within the raised wall 200 are not visible through the translucent portion 114 when the light emitting device 300 is illuminated. The majority (e.g., over 60% or over 75%) of the height of the translucent portion 114 is translucent to allow the light emitted by the light emitting device 300 to be visible through the translucent portion 114. The PCB is configured to cause the light emitting device 300 to periodically or randomly change an intensity or brightness output of light emitted by the light emitting device 300 to create a flickering effect through the translucent portion 114.

The PCB can be configured to adjust or vary a speed of the fan 310 or an on/off duty cycle of the fan 310 to reduce power consumption from the power source 302. The speed or duty cycle can be adjusted to reduce power based on, e.g., time of day or expiration of a timer since the fan 310 was turned on. Additionally, or alternately, the PCB can be configured to turn off the fan 310 even when the switch 122 is in the first or second mode, in response to detecting that a current or a voltage of the power source 302 falls below a predetermined threshold, e.g., a threshold voltage depending on the type of power source 302.

Figure 4:
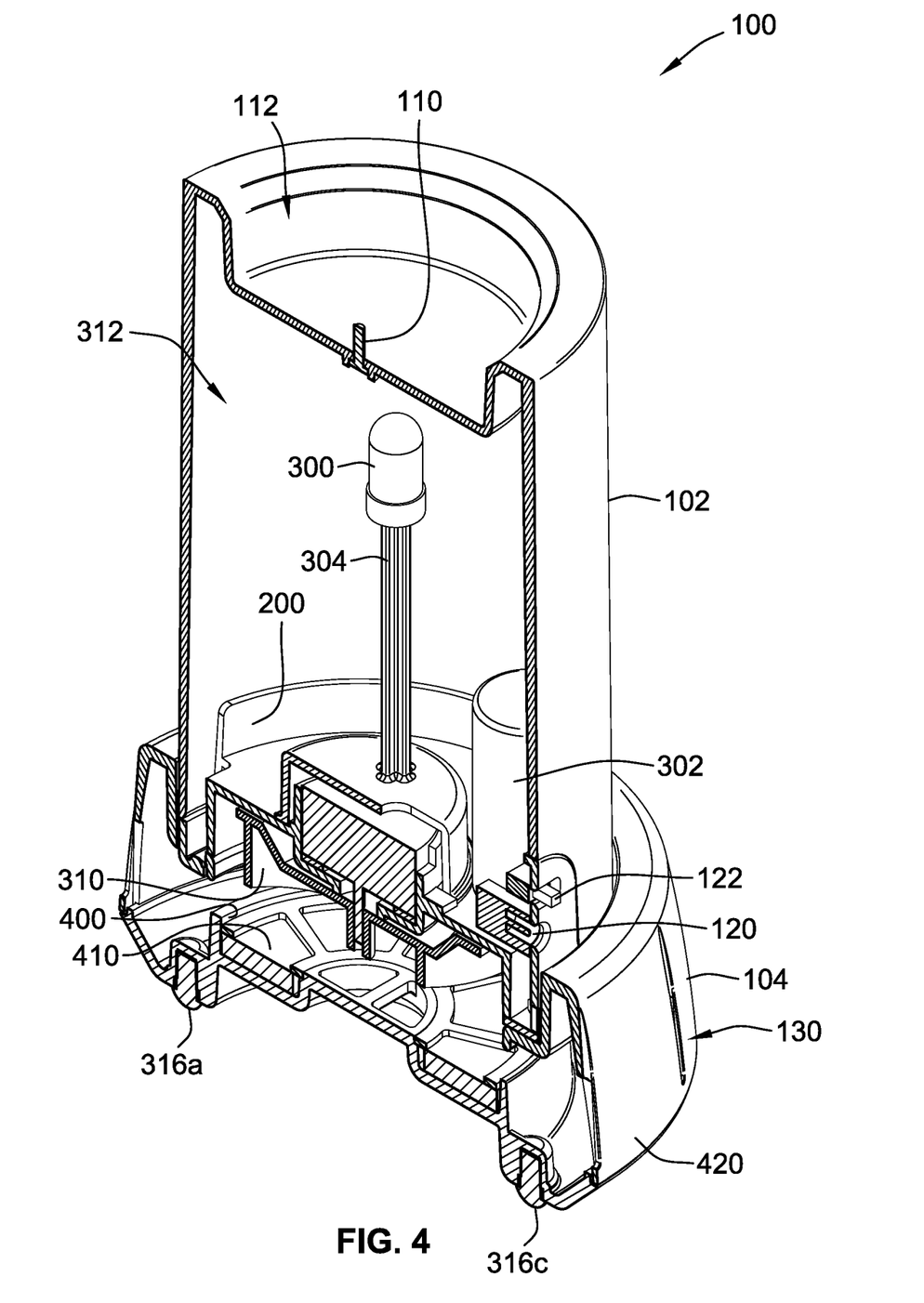
FIG. 4 is an isometric view of the cross section of the candle shown in FIG. 3.

Returning to the base portion 104, it further includes a fan 310 coupled to the PCB and powered by the power source 302. The fan 310 is turned by a motor 702 (best seen in FIG. 7). The fan 310 is oriented to force air in a downwards direction (towards earth) and away from the body portion 104. There is a pad 410 (best seen in FIGS. 4 and 9), such as a felt pad, configured to receive upon a surface thereof a fragrance or scent. The fragrance or scent can be infused into the pad and/or can be added externally to the pad in a liquid or semi-liquid form. The pad 410 is positioned below the fan 310 such that the forced air from the fan 310 moves toward the pad 410. The pad 410 can include a felt material and has a generally thin, donut shape as seen in FIG. 7, and can be secured between a tray or other receptacle 710 and a retaining disc 400 with openings to expose the corresponding portions of the pad 410 to the forced air created by the blades 602 of the fan 310.

Figure 6:
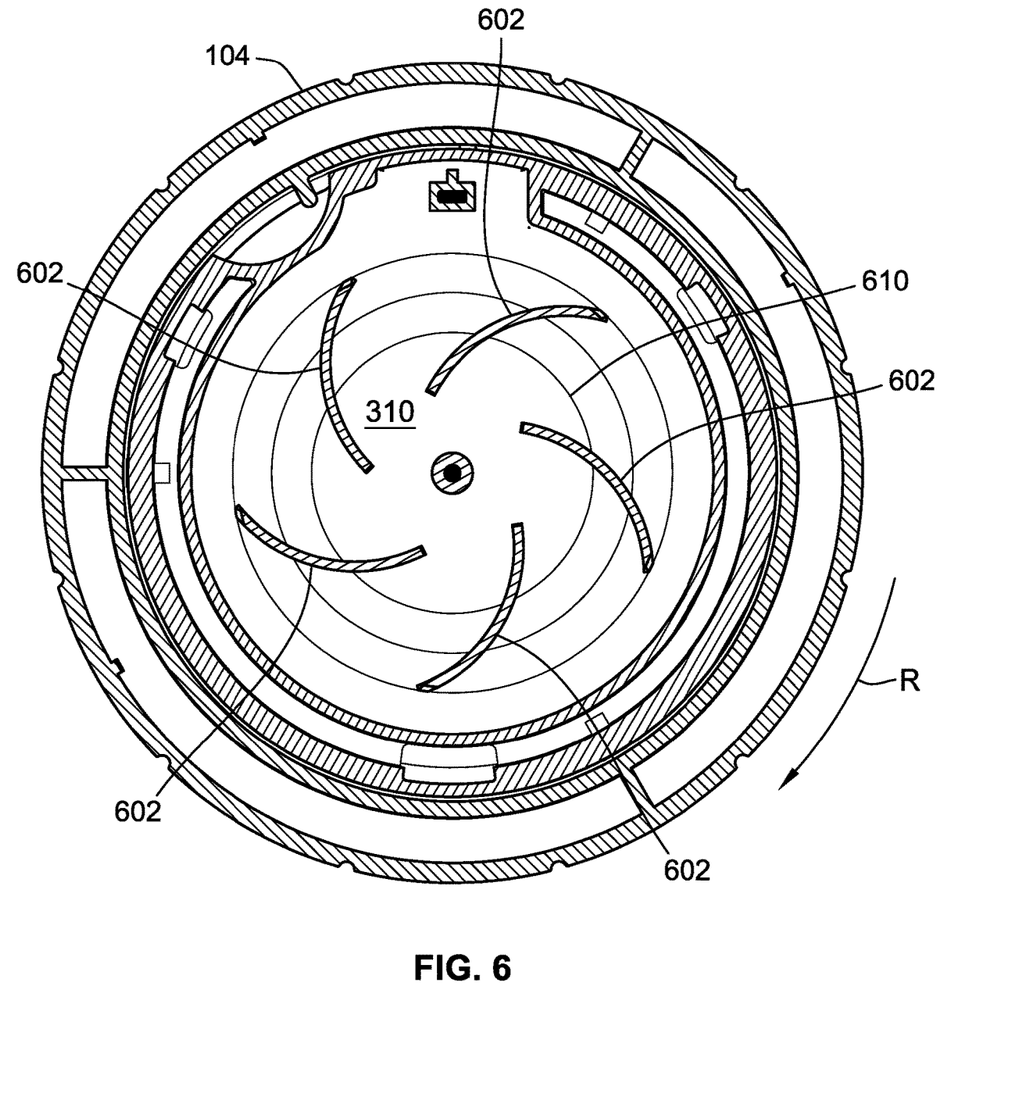
FIG. 6 is a bottom view of the base portion in which a fan and its blades are exposed.

FIG. 6 illustrates a bottom view of the base portion 104 with the fan 310 exposed to show fan blades 602 arranged on a fixed portion 610 to direct or force air away from the base portion 104 and in a direction toward earth. The fan blades 602 rotate in a direction R shown in FIG. 6 and can be curved or shaped to facilitate air flow in the direction R. Stated another way, the fan 310 includes fan blades 602 arranged on a bottom surface 610 (see FIG. 6) of a fixed portion of the fan 310 to direct air away from the fixed portion 610 toward a bottom of the base portion 104. A bottom plate or tray 710 (best seen in FIG. 7) forces the air to change direction approximately 90 degrees and escape through a wall 420 (see FIG. 4) of the base portion 104 via a plurality of openings 130, having been infused with the scent of the fragrance prior to escaping through the openings 130. Stated another way, the air moved by the fan 310 is configured to travel in a first direction A (FIG. 3) from the fan 310 toward the pad 410, strike the pad 410, and change direction to a second direction B before exiting the openings 130. The first direction A is generally orthogonal to the second direction B. The openings 310 are spaced (optionally equidistantly) around a periphery of the base portion 104 so that the air exits the base portion 104 to create a 360 degree fragrance field around the candle 100.

Figure 5:
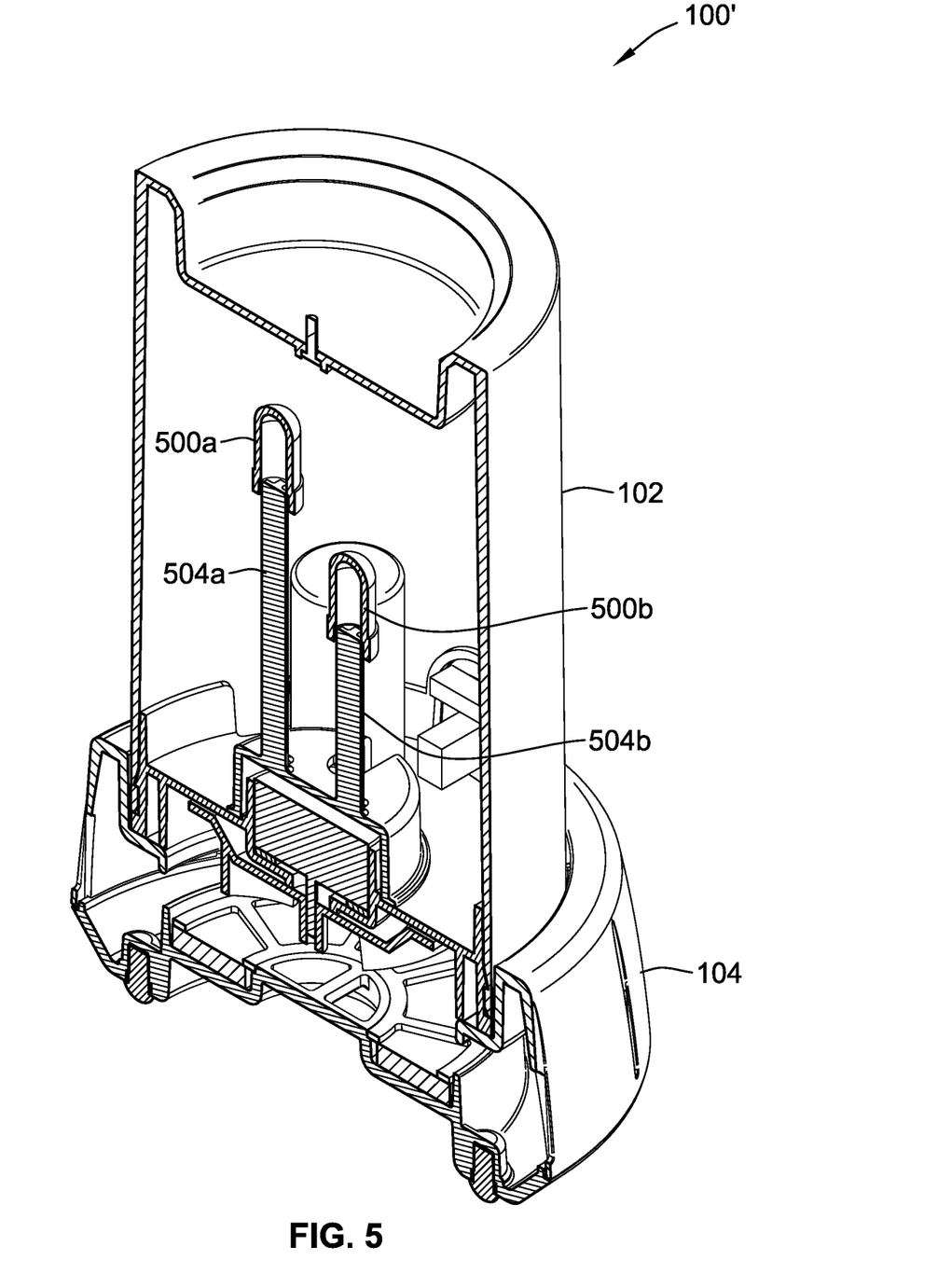
FIG. 5 is an isometric view of the cross section of a candle according to another embodiment having two light emitting devices.
Figure 7:
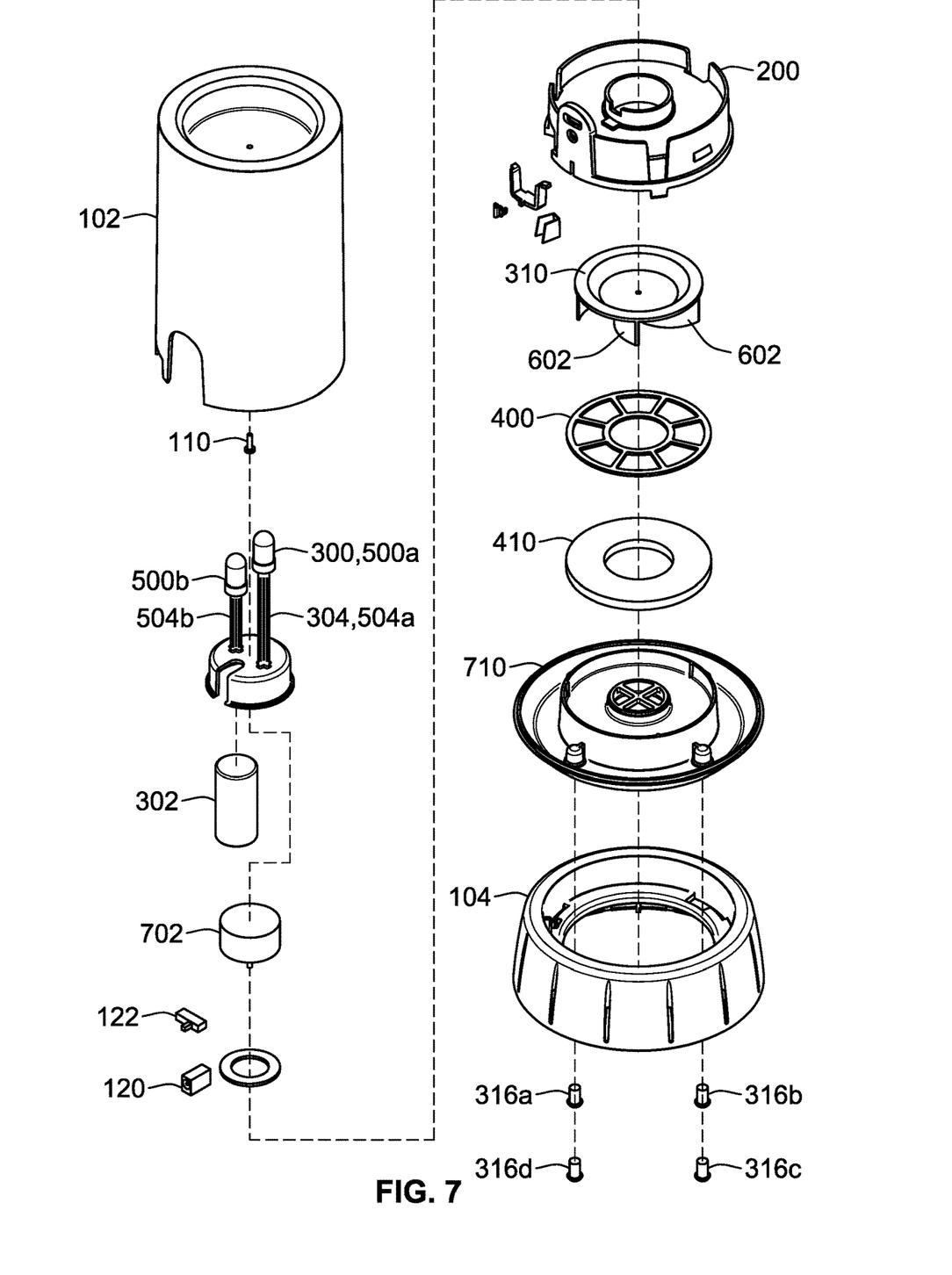
FIG. 7 is an exploded, isometric view of some parts that form the candle shown in FIG. 5.

It should be noted that although the exploded view of the parts shown in FIG. 7 illustrate a candle having two light emitting devices shown in FIG. 5, the same parts are present in the embodiment shown in FIGS. 1-6, except that instead of two light emitting devices, there is one light emitting device 300 and one supporting post 304.

The switch 122 is selectable among one of a plurality of modes that affect operation of the light emitting device(s) and/or the fan. The modes can include a first mode wherein the light emitting device 300 and the fan 310 are both turned on, an off mode wherein neither the light emitting device 300 nor the fan 310 is turned on, and a second mode wherein one of the light emitting device 300 or the fan 310 but not both is turned on. Additional modes are contemplated, e.g., a third mode in which the light emitting device 300 changes between a steady or a flickering light effect, and a fourth mode that adjusts a speed of the fan 310. The switch 122 can include more than one switch or button or any other interface to allow a user of the candle 100 to change an operating mode of the candle 100 by interacting with the interface.

Figure 3:
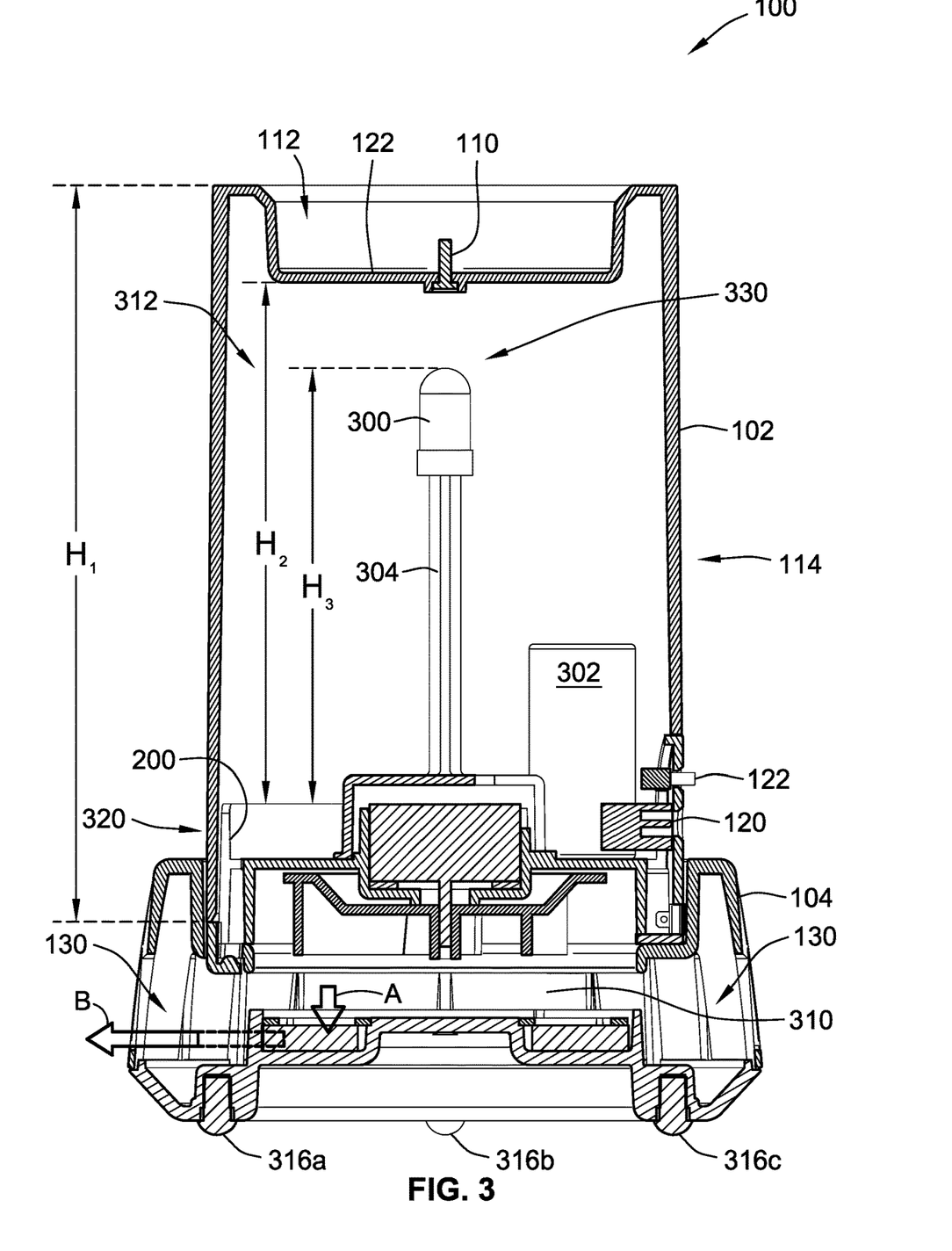
FIG. 3 is a cross-section of the candle shown in FIG. 1 showing the body portion and the base portion and respective components therein.

The base portion 104 further includes a post 304 (FIG. 3) arranged in approximately the center of the base portion 104 as shown in FIG. 3. The light emitting device 300 is positioned on the post 304 so that the light emitting device 304 is positioned in a generally central area 330 inside the body portion 102 at a height corresponding to a height, H3, of the post 304. The height, H3, is preferably selected so that the light emitting device 304 is positioned between 25-90% of the available interior height space inside the housing 140. In FIG. 3, the light emitting device 300 is positioned approximately at a distance representing 75% of the available interior 312 height space. Other ways of securing the light emitting device 300 inside the interior 312 of the housing 140 are also contemplated; however, the post 304 has the advantage of being relatively imperceptible through the translucent portion 114 of the housing 140.

The post 304 shown in FIG. 3 is fixed, but in another embodiment, the post 304 is flexible enough to sway from side to side, or is secured to a fixed part of the body or base portion 102, 104 by a flexible mechanism, such as a spring. In this embodiment, the fan 310 can be deliberately rotationally unbalanced slightly to cause the post 304 to wobble as the fan 310 rotates, thereby inducing the post 304 to sway or undulate from side to side, creating a dynamic lighting effect via the translucent portion 114 of the body portion 102.

The candle 100 can further include a wick element 110 (FIG. 1) extending away from a top portion 122 of the body portion 102. Light emitted by the light emitting device 300 appears to emanate from within the interior 312 of the body portion 102. The wick element 110 is arranged in a recess portion 112 of the body portion 102 such that the top portion away from which the wick element 110 extends is located a distance below a top surface 122 of the body portion 102.

The power source 302 can be a rechargeable Lithium-Ion battery. The base portion 102 includes a power charging interface 120 configured to receive a plug (not shown) for recharging the battery 302 from an external power supply (not shown). The base portion 102 includes a twist and lock feature 202, 204 (FIG. 2) to removably secure the base portion 102 and the body portion 104.

Figure 2:
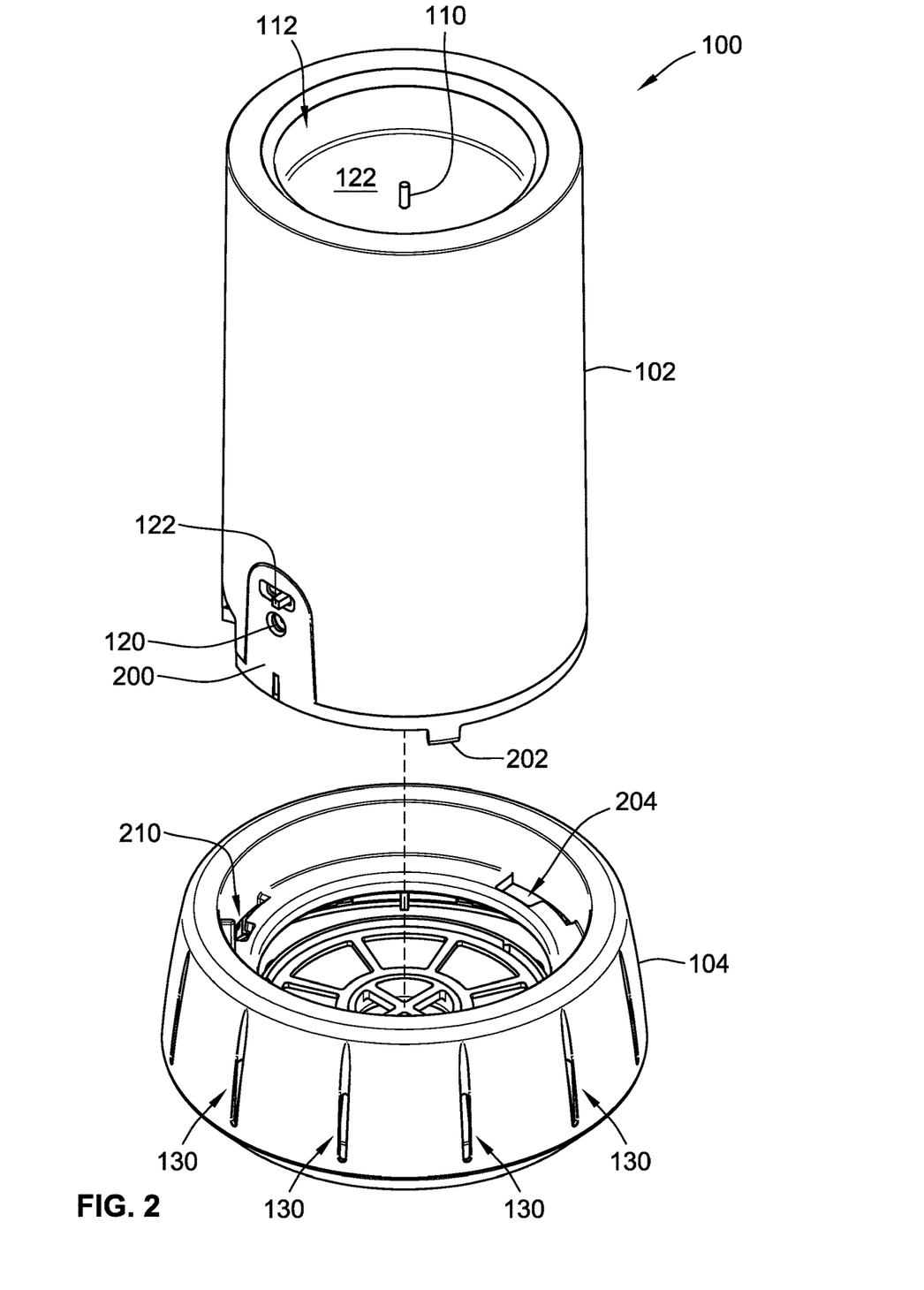
FIG. 2 is a perspective view of the candle shown in FIG. 1 with the body portion mated with the base portion.

The candle 100 can further include a safety switch 210 arranged to change states in response to the twist and lock feature 202, 204 being engaged, the change of states causing energy to be supplied or stopped from the power source 302.

Four rubber feet 316*a,b,c,d* (best seen in FIG. 7) provide a stable grip on the resting surface, and also minimize or suppress vibrations and transmitted noise from the fan 310 onto the surface for quiet operation of the candle 100.

A candle 100' shown in FIG. 5 is the same as the candle 100 shown in FIG. 1 except that there is a second light emitting device 500*b* in addition to a first light emitting device 500*a*, for additional brightness and flickering options. The PCB is configured to provide power from the power source 302 to one or both of the light emitting device 500*a* and the second light emitting device 500*b*.

The base portion 104 shown in FIG. 5 further includes a first post 504*a* arranged in the center of the base portion 104. The light emitting device 500*a* is positioned on the first post 504a so that the light emitting device 500a is positioned in a generally central area inside the body portion 102 at a height corresponding to a height of the first post 504a. The base portion 104 includes a second post 504b on which the second light emitting device 500b is positioned. The first post 504a has a different height relative to the second post 504b so that the light emitting device 500a and the second light emitting device 500b are at different heights within the base portion 104.

Figure 8:
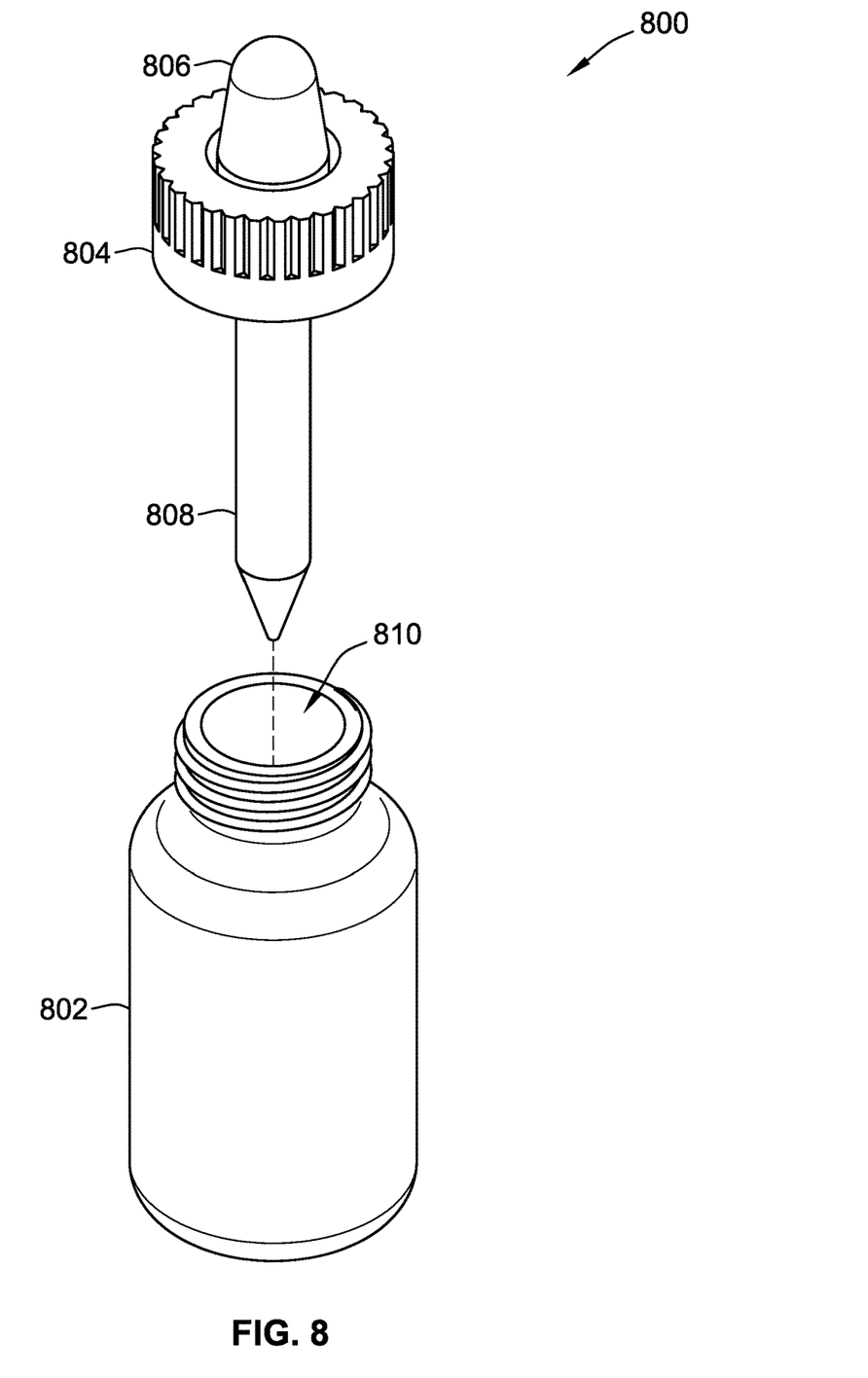
FIG. 8 is a perspective view of an eye dropper bottle and pipette containing a fragrance or scent in liquid or oil-based form.

FIG. 8 illustrates a container 800 that can be combined with the candle 100, 100', and which contains a fragrance or scent. While the container 800 is shown as a bottle container and eyedropper, other form factors can include a cartridge or any substrate configured to hold a fragrance or scent. In FIG. 8, the container 800 contains the fragrance or scent incorporated into an oil-based liquid 810. The container 800 including an eye dropper 804 having a pipette 808 and a squeezable bulb 806 to draw the oil-based liquid into the pipette by squeezing the bulb and to release the oil-based liquid 810 from the eye dropper 804 by releasing the bulb 806 after squeezing it to draw some of the liquid 810 temporarily up into the pipette 808.

Figure 9:
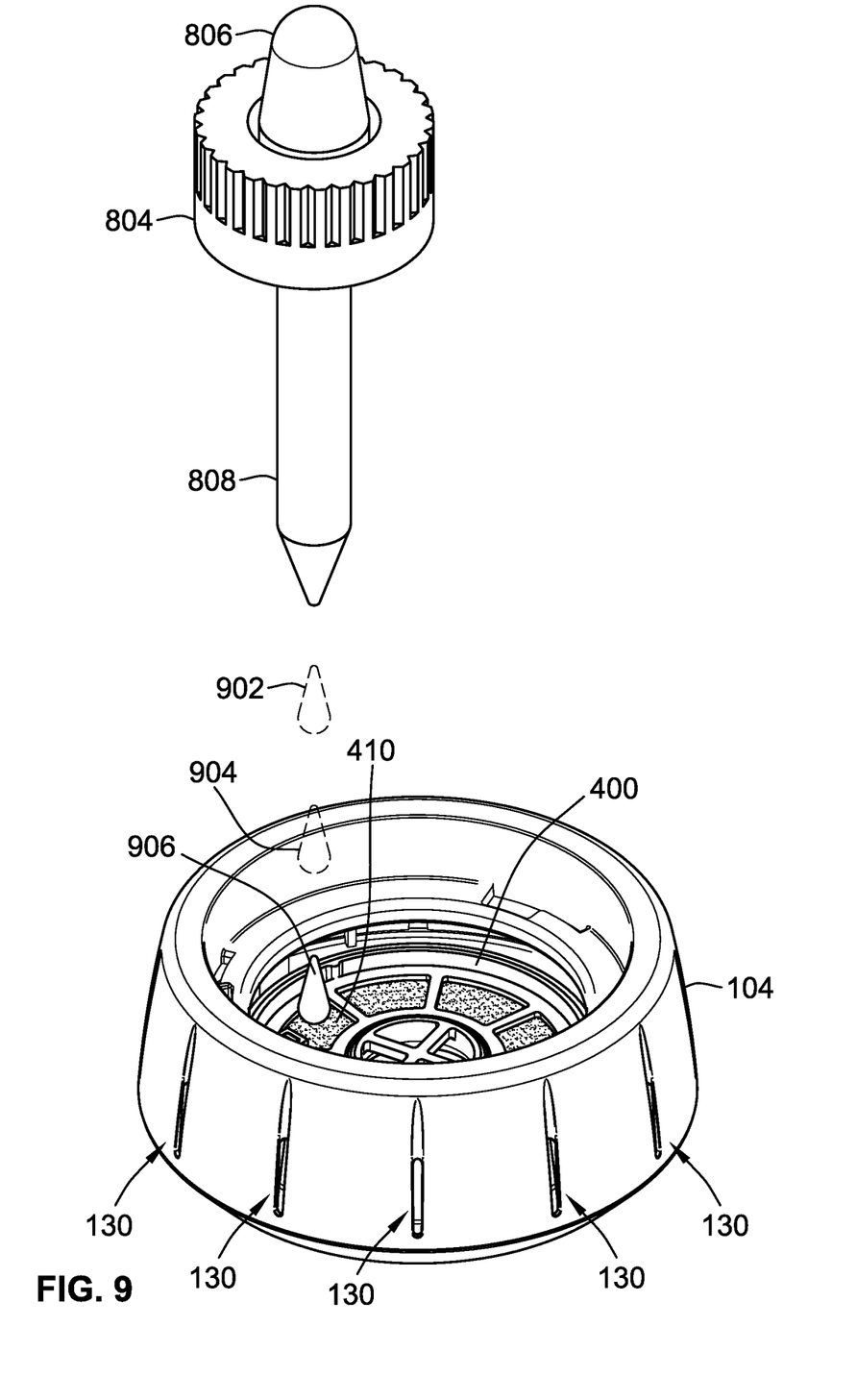
FIG. 9 illustrates an isometric view of the pipette shown in FIG. 8 dispensing drops of the fragrance or scent onto an exposed pad of a base portion of a candle disclosed herein.

FIG. 9 illustrates an exploded, partial view, with the body portion 102 removed, of an exposed base portion 104 and the eye dropper 804 positioned to dispense the scent or fragrance onto the pad 410 in the base portion 104, without removing the pad 410 or any other component of the base portion 104. Reversing the twist and lock feature 202, 210 allows the user to remove the base portion 102 from the body portion 104, to reveal an exposed surface of the pad 410 below the fan 310. The user positions the pipette 808 over the pad 410 and squeezes the pipette 808 to allow drops 902, 904, 906 of the scent or fragrance in liquid form to fall onto the pad 410. The user can move the pipette 808 around the pad 410 to squeeze a drop or two from the pipette 808 of fragrance or scent in an approximately uniform distribution around the pad 410. Uniform distribution is not necessary, and the amount of fragrance or scent dispensed can depend upon the intensity of the desired fragrance or scent to be dispensed from the candle 100 when the fan 310 is operated. The pad 410 is removable and replaceable, as is the fragrance or scent in the bottle container 800, allowing the user to enjoy different fragrances or scents while illuminating the candle 100.

The combination of an interiorly illuminated candle and a silent, hidden fan that dispenses a fragrance or scent from the candle creates a clean visual and olfactory effect. When a battery is used as the power source 302, the candle 100, 100' is fully portable and can be placed anywhere a traditional candle could be placed and areas where a traditional candle cannot or should not be placed, such as near drapes or other flammable materials. The user has the ability to add more fragrance or scent to the pad 410, creating a very long life candle. Power-saving strategies can be used to reduce the power consumption by the fan 310.

Importantly, to create the illusion of a glowing fire inside the candle body, most of the interior space inside the candle is empty, so that electronics, wires, and other internal components are not visible when the light emitting device is illuminated. A band of opaque areas can be seen on the top and bottom of the candle, e.g., about top and bottom 5%, but the majority of the elongated candle housing, e.g., about 90% or greater than 80% or greater than 70% is translucent. The illumination of the internal light emitting device does not create from observing the exterior of the candle any internal shadows or visible artifacts inside the candle. Components and wires are hidden in the base portion of the candle so as not to be visible through the body portion. The body portion is composed of a single, unitary cylindrical-shaped housing having a single wall made of a translucent material that resembles a wax candle. The ratio of the height of the body portion relative to the base portion is about 2:1 or 3:1 or 4:1. In the schematic shown in FIG. 3, H1 refers to the overall height of the body portion 102, H2 refers to the visible height along which light is visible from the light emitting device 300 through the body portion 102, and H3 refers to the height of the light emitting device from the base of H2 to the top of the post 304. Because the light emitting device is positioned inside the body of the candle, its emitted light will also create a shadow or dark outline of any structure inside the cavity in which the light emitting device is placed. The present disclosure optimizes the illuminated real estate on the exterior of the candle as much as possible by keeping nearly all of the interior of the body portion of the candle empty except for the light emitting device so that when viewed externally and the light emitting device is turned on, the user visually perceives a glowing candle body that seems to burn from inside the body. If any internal components were visible, or were to create any shadows, the visual continuity would be disrupted.

Moreover, the fan drives the air toward the base of the candle away from the light emitting device so that the air exits circumferentially the base portion of the candle. Openings spaced, e.g., equidistantly, around the periphery of the base portion allow the fragrance or scent to permeate around the entire periphery of the candle, creating a 360 degree fragrance field around the base of the candle, pushing scented air around the candle's base into the outside environment, not toward the top of the candle or through its body. No heating element is involved in driving scent from the candle. The scent is driven away from the base solely by a fan without heating the fragrance or any substrate containing the fragrance. When a battery is used, the candle is fully portable and does not need to be near an outlet during operation, except when the battery is recharged.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A flameless electric candle having a fan-driven scent diffuser, comprising:
    a body portion having a translucent portion and a generally elongated cylindrical shape and housing therein a light emitting device configured to permit its emitted light to be partially visually discernible through the translucent portion, the body portion further including a second light emitting device;
    a base portion below the body portion, the base portion including:
    an electronics module having a printed circuit board (PCB), a switch, the light emitting device, and a power source configured to supply power to the PCB and the light emitting device, the PCB being configured to provide power to one or both of the light emitting device and the second light emitting device;

a fan coupled to the PCB and powered by the power source, the fan being oriented to force air in a downwards direction away from the body portion;

a pad configured to receive upon a surface thereof a fragrance or scent, the pad being positioned below the fan such that the forced air moves toward the pad;

a plurality of openings in a wall of the base portion to allow the forced air scented by the fragrance or sent to escape the base portion, the switch being selectable among one of a plurality of modes, the modes including a first mode wherein the light emitting device and the fan are turned on, an off mode wherein neither the light emitting device nor the fan is turned on, and a second mode wherein one of the light emitting device or the fan is turned on, wherein the base portion further includes a first post arranged in the center of the base portion, the light emitting device being positioned on the first post so that the light emitting device is positioned in a generally central area inside the body portion at a height corresponding to a height of the first post, and wherein the base portion includes a second post on which the second light emitting device is positioned, the first post having a different height relative to the second post so that the light emitting device and the second light emitting device are at different heights within the base portion.

2. The candle of claim 1, wherein the base portion includes a wall portion that contains the PCB and the power source so that when the light emitting device is emitting light, neither the PCB nor the power source is visible through the translucent portion.

3. The candle of claim 1, wherein the base portion further includes a post arranged in the center of the base portion, the light emitting device being positioned on the post so that the light emitting device is positioned in a generally central area inside the body portion at a height corresponding to a height of the post.

4. The candle of claim 3, wherein the post is flexible to sway from side to side, and the fan is rotationally unbalanced to cause the post to wobble as the fan rotates, thereby inducing the post to sway or undulate from side to side, creating a dynamic lighting effect via the translucent portion of the body portion.

5. The candle of claim 1, wherein the PCB is configured to cause the light emitting device to periodically or randomly change an intensity or brightness output of light emitted by the light emitting device to create a flickering effect through the translucent portion.

6. The candle of claim 1, further comprising a wick element extending away from a top portion of the body portion, with light emitted by the light emitting device appearing to emanate from within the interior of the body portion.

7. The candle of claim 6, wherein the wick element is arranged in a recess portion of the body portion such that the top portion away from which the wick element extends is located a distance below a top surface of the body portion.

8. The candle of claim 1, wherein the power source is a rechargeable Lithium-Ion battery, the base portion further including a power charging interface configured to receive a plug for recharging the battery from an external power supply.

9. The candle of claim 1, wherein the PCB is further configured to adjust a speed of the fan or a duty cycle of the fan to reduce power consumption from the power source.

10. The candle of claim 1, wherein the base portion includes a twist and lock feature to removably secure the base portion and the body portion.

11. The candle of claim 10, further comprising a safety switch arranged to change states in response to the twist and lock feature being engaged, the change of states causing energy to be supplied or stopped from the power source.

12. The candle of claim 11, wherein the PCB is configured to turn off the fan even when the switch is in the first or second mode, in response to detecting that a current or a voltage of the power source falls below a predetermined threshold.

13. The candle of claim 1, wherein the plurality of modes further including a third mode that determines whether light emitted by the light emitting device is steady or is made to appear to flicker.

14. The candle of claim 1, in combination with a container, cartridge, or substrate containing the fragrance or scent.

15. The candle of claim 14, wherein the container or cartridge contains the fragrance or scent incorporated into an oil-based liquid.

16. The candle of claim 14, in combination with the container, the container including an eye dropper having a pipette and a bulb to draw the oil-based liquid into the pipette by squeezing the bulb and to release the oil-based liquid from the eye dropper by releasing the bulb.

17. The candle of claim 16, wherein the pad includes a felt material and has a generally thin, donut shape.

18. The candle of claim 1, wherein the air moved by the fan is configured to travel in a first direction from the fan toward the pad, strike the pad, and change direction to a second direction before exiting the plurality of openings, the first direction being generally orthogonal to the second direction, and the plurality of openings being spaced around a periphery of the base portion so that the air exits the base portion to create a 360 degree fragrance field around the candle.

19. The candle of claim 1, wherein the fan includes a plurality of fan blades arranged on a bottom surface of a fixed portion of the fan to direct air away from the fixed portion toward a bottom of the base portion.

* * * * *